United States Patent [19]

Kaneko et al.

[11] Patent Number: 5,013,851
[45] Date of Patent: May 7, 1991

[54] INTERMEDIATES FOR THE PRODUCTION OF PODOPHYLLOTOXIN AND RELATED COMPOUNDS

[75] Inventors: Takushi Kaneko; Henry S. L. Wong, both of Fayetteville, N.Y.

[73] Assignee: Bristol-Myers Company, New York, N.Y.

[21] Appl. No.: 304,634

[22] Filed: Feb. 1, 1989

Related U.S. Application Data

[62] Division of Ser. No. 129,795, Dec. 7, 1987, Pat. No. 4,845,248, which is a division of Ser. No. 805,484, Dec. 5, 1985, Pat. No. 4,734,512.

[51] Int. Cl.$^5$ ............................................ C07D 407/04
[52] U.S. Cl. ..................................... 549/298; 549/300
[58] Field of Search ................................ 549/300, 298

[56] References Cited

U.S. PATENT DOCUMENTS 4,294,763  10/1981  Kende et al. .......................... 549/433
4,391,982   7/1983  Kende et al. .......................... 549/433
4,644,072   2/1987  Vyas et al. ............................ 549/433

Primary Examiner—Nicky Chan
Attorney, Agent, or Firm—Aldo A. Algieri

[57] ABSTRACT

There are disclosed intermediates which can be converted into podophyllotoxin and related compounds, which are known antineoplastic agents. There are also disclosed processes for the preparation of such intermediates, and processes for the conversion of the intermediates into known intermediates which are readily converted into podophyllotoxin and related compounds.

2 Claims, No Drawings

INTERMEDIATES FOR THE PRODUCTION OF PODOPHYLLOTOXIN AND RELATED COMPOUNDS

CROSS-REFERENCE TO RELATED APPLICATIONS

This application is a division of our co-pending application Ser. No. 129,795 filed Dec. 7, 1987, U.S. Pat. No. 4,845,248, which is a division of our application Ser. No. 805,484 filed Dec. 5, 1985, issued as U.S. Pat. No. 4,734,512.

BACKGROUND OF THE INVENTION

1. Field of the Invention

The present invention is directed to intermediates which can be converted into podophyllotoxin and related compounds, which are known antineoplastic agents. More specifically, this invention relates to an efficient total synthesis of podophyllotoxin. Additionally, the present invention provides processes for the preparation of such intermediates, and processes for the conversion of the intermediates into known intermediates which are readily converted into podophyllotoxin and related compounds.

2. Description of the Prior Art

Podophyllotoxin (I), a known lignan lactone isolated from several species of Podophyllum, is a potent cytotoxic agent. Numerous other related compounds having the characteristic aryltetralin ring structure, either naturally occurring or derived from some naturally occurring compounds are known. Some of these compounds possess antineoplastic activity while others are useful for conversion to compounds having such activity. Podophyllotoxin is an important intermediate for the production of the antitumor agent etoposide and its analogues. Podophyllotoxin has the structure shown below:

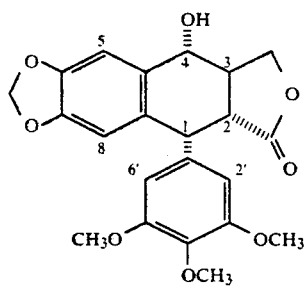

I

The key molecular features of podophyllotoxin are (1) presence of the C2-C3 trans lactone, and (2), a cis relationship between the C1 and C2 substituents. For the synthesis of etoposide, the C4 hydroxy group can be either in the α (podophyllotoxin) or the β (epipodophyllotoxin) orientation because in the glycosidation step only the C4 β glycoside is obtained.

In *J. Org. Chem.*, 31, 4004–4008 (1966), W. J. Gensler and C. D. Gatsonis describe the completion of the total synthesis of podophyllotoxin through the epimerization by enolate quenching of the O-tetrahydropyranyl derivative of picropodophyllin. However, this epimerization does not proceed to completion, and separation of an about 45:55 mixture of podophyllotoxin and picropodophyllin is required. Picropodophyllin which is the cis-lactone isomer of podophyllotoxin has the structure:

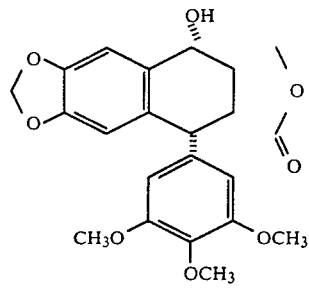

II

In *J. Org. Chem.*, 46, 2826–2828 (1981), A. S. Kende et al. report on an improved total synthesis of podophyllotoxin in 12 steps with an overall yield of 4.5% from piperonal. However, the Kende synthesis requires the preparation and then the subsequent epimerization of picropodophyllin similar to the above-mentioned Gensler synthesis.

In *J. Am. Chem. Soc.*, 103, 6208–6209 (1981), D. Rajapaksa and R. Rodrigo report a new synthesis of podophyllotoxin which avoids the thermodynamic hurdle present in the conversion of picropodophyllin to podophyllotoxin as was previously described in the above-mentioned references of Gensler et al. and Kende et al. However, the synthesis requires the preparation of a bicyclic precursor and a satisfactory yield can be achieved only by recycling procedures.

SUMMARY OF THE INVENTION

The preparation of podophyllotoxin in accordance with the present invention also avoids the picropodophyllin intermediate and, in addition, provides a new and efficient stereospecific synthesis starting with Gensler ketone of the formula:

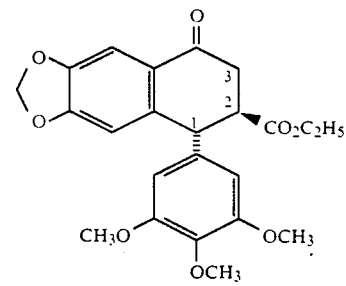

This invention is based on the realization that the cis Gensler ketone of the formula

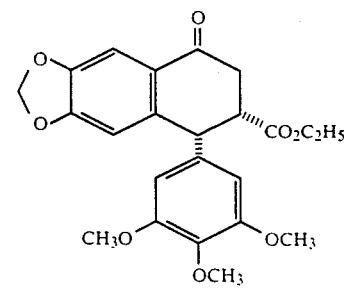

has a finite stability. This stability permits the incorporation of a hydroxymethyl group at C3 without epimerization at C2.

Previously, Kende et al, [*J. Amer. Chem. Soc.*, 99, 7082-7083 (1977) and *J. Org. Chem.*, 46, 2826-2828 (1981)] and Murphy et al [*J. C. S. Perkins* I, 271-276 (1982)] have tried hydroxymethylation at C3 using a base and formaldehyde. This gave mainly the bisalkylation product and the yield was not high. The present invention avoids bisalkylation, and gives a product with the desired stereochemistry at C2.

The synthesis of podophyllotoxin and related compounds in accordance with this invention is depicted in Scheme I:

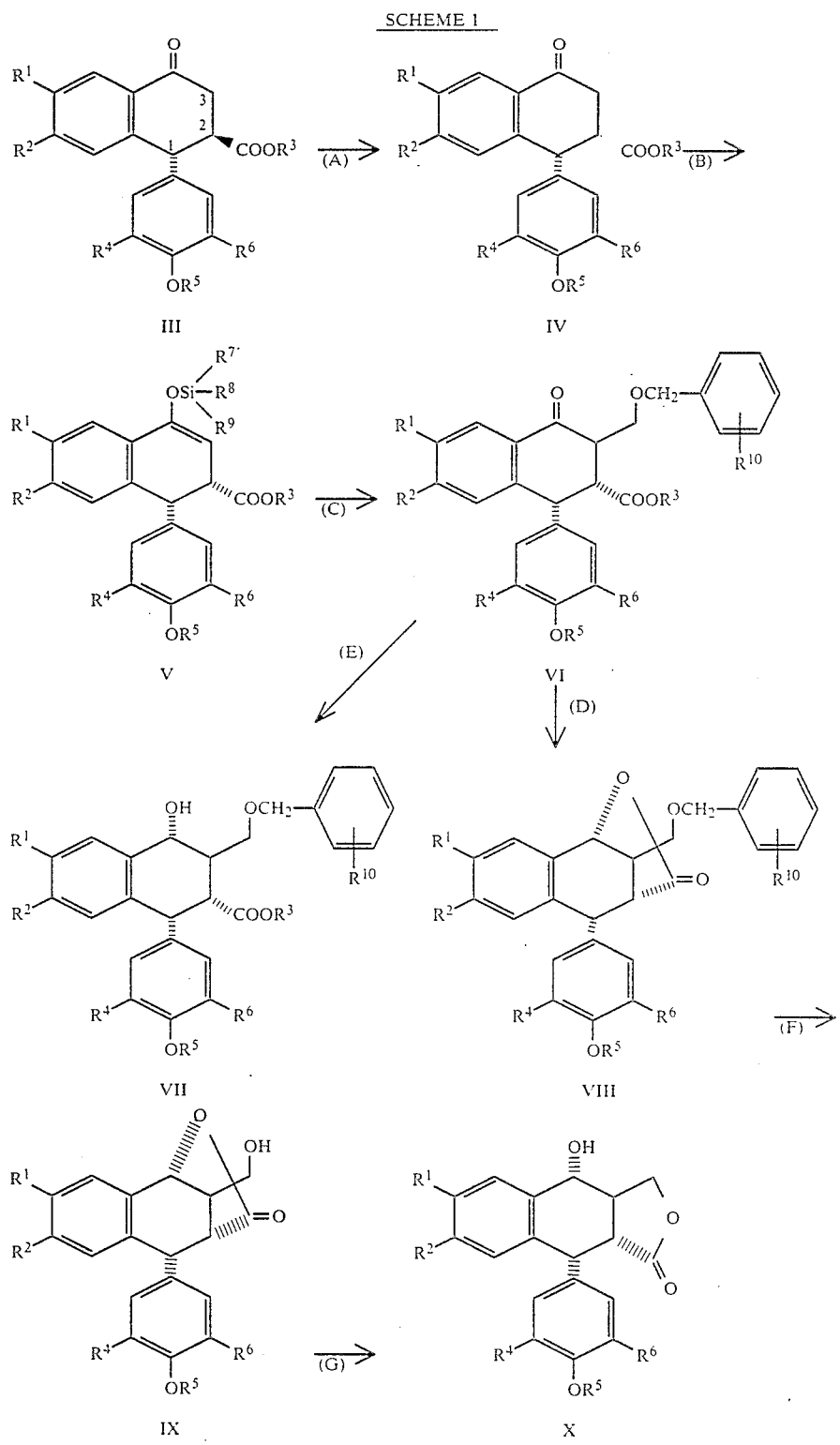

wherein $R^1$ and $R^2$ each are independently hydrogen or (lower)alkoxy, or $R^1$ and $R^2$, taken together, is methylenedioxy; $R^3$ is hydrogen or a carboxyl-protecting group; $R^4$ and $R^6$ each are independently hydrogen or (lower)alkoxy; $R^5$ is hydrogen or a phenol-protecting group; $R^7$, $R^8$ and $R^9$ each are independently lower(alkyl) or phenyl; and $R^{10}$ is hydrogen, lower(alkyl), lower(alkoxy) or nitro.

Compounds V, VI, VII and VIII in Scheme I are novel intermediates.

The terms "(lower)alkyl" and "(lower)alkoxy" as used herein and in the claims mean unbranched or branched chain alkyl or alkoxy groups containing from 1 to 6 carbon atoms such as methyl, ethyl, propyl, isopropyl, butyl, isobutyl, t-butyl, amyl, hexyl, etc. Preferably, these groups contain from 1 to 4 carbon atoms and, most preferably, they contain 1 or 2 carbon atoms. Unless otherwise specified in the particular instance, the term "halogen" as used herein and in the claims is intended to include chlorine, fluorine, bromine and iodine.

Carboxyl-protecting groups which can be employed in the present invention to block or protect the carboxylic acid function are well-known to those skilled in the art and include moieties such as (lower)alkyl, phenyl(lower)alkyl, ring substituted phenyl(lower)alkyl, methoxymethyl, benzyloxymethyl, allyl, diphenylmethyl and the like. Phenol-protecting groups which can be employed in the present invention to block or protect the phenol function are also well-known to those skilled in the art and include moieties such as (lower)alkyl, phenyl(lower)alkyl, ring substituted phenyl(lower)alkyl, benzyloxycarbonyl, 2,2,2-trichloroethoxycarbonyl, methoxymethyl, allyl and the like. Other suitable protecting groups are disclosed in "Protective Groups in Organic Synthesis", Theodora W. Greene (John Wiley & Sons, 1981), Chapter 3 for phenol and Chapter 5 for carboxyl, which are hereby incorporated by reference.

DETAILED DESCRIPTION OF THE INVENTION

The aryltetralone starting material, a compound of Formula III, wherein $R^1$ and $R^2$, taken together, is methylenedioxy, $R^3$ is hydrogen, $CH_3$ or $C_2H_5$, $R^4$ and $R^6$ are methoxy, and $R^5$ is methyl may be prepared by the general method described in *J. Am. Chem. Soc.*, 82, 1714–1727 (1960), W. J. Gensler et al. Compounds of Formula III may also be prepared by an improved procedure described in *J. C. S. Perkin* I, 271–276 (1982), W. S. Murphy and S. Wattanasin, in which $R^1$ is methoxy and $R^2$ is hydrogen, or $R^1$ and $R^2$, taken together, is methylenedioxy, $R^3$ is hydrogen or ethyl, $R^4$ and $R^6$ are hydrogen or $R^4$ and $R^6$ are methoxy, and $R^5$ is methyl.

A compound of Formula III, with the ester radical in the relative trans configuration, is epimerized to a cis aryltetralone of Formula IV at low temperatures, i.e., from about $-80°$ C. to $-20°$ C., and preferably at about $-78°$ C., by enol quenching utilizing a non-nucleophilic strong base such as lithium hexamethyldisilazide, sodium methylsulfinylmethide, lithium 1,1,6,6-tetramethylpiperide and lithium diisopropylamide in an inert organic solvent such as tetrahydrofuran (THF), dioxane, dimethoxymethane, hexamethylphosphoramide and tetramethylurea and then adding a mineral acid, for example, hydrochloric acid. This is reaction A of Scheme I.

Reaction B of Scheme I illustrates the preparation of the enol silyl ether, a compound of Formula V, from a compound of Formula IV. This is accomplished by reacting a compound of Formula IV with a reagent having the formula:

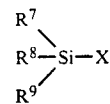

wherein $R^7$, $R^8$, and $R^9$ are as previously defined and X is a halogen atom or a trifluoromethanesulfonate group. The reaction is conducted at a temperature of from $-78°$ C. to 25° C. in the presence of a non-nucleophilic base. To avoid epimerization at C2, the mildest possible conditions should be employed. The silyl reagent XI may be, for example, trimethylsilyl trifluoromethanesulfonate (TMSOTf), trimethylsilyl iodide, t-butyl-dimethylsilyl iodide or triethylsilyl iodide.

A compound of Formula V may be converted to a compound of Formula VI, reaction C in Scheme I, without purification or isolation of a compound of Formula V. This is accomplished by reacting a compound of Formula V with a bisbenzyloxymethane having the formula:

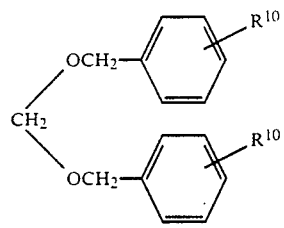

or a benzyloxymethyl halide having the formula:

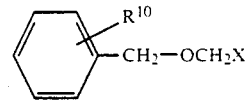

wherein $R^{10}$ is the same as previously described and X is halogen. This reaction is conducted in the presence of a Lewis acid such as TMSOTf, $ZnCl_2$, $ZnBr_2$, and $TiCl_4$. The reaction should be conducted at a temperature of from about $-50°$ C. to 20° C. and preferably at about 0° C.

A compound of Formula VI is converted to a compound of Formula VIII by reduction of the C4 carbonyl group at a temperature of from $-20°$ C. to 20° C. using a reducing agent such as $LiBH_4$, $NaBH_4$, $NaBH_3CN$, $LiBHC_2H_5$, or $Zn(BH_4)_2$. Compounds of Formula VII are obtained as a by-product of this reaction.

Reaction F of Scheme I illustrates the debenzylation of a compound of Formula VIII to obtain a compound of Formula IX. Debenzylation can be carried out by standard hydrogenating conditions, i.e., by using catalysts such as Pt, Raney Ni, Rh and solvents such as THF, ethanol and ethyl acetate. This reaction is carried out at a temperature of from 0° C. to 50° C., preferably about 25° C.

A compound of Formula IX is converted to a compound of Formula X (Reaction G of Scheme I) by treatment with an aqueous base followed by treatment with a condensation reagent, e.g., dicyclohexylcarbodiimide, 1-cyclohexyl-3-(2-morpholinoethyl)-carbodiimide metho-p-toluenesulfonate, isopropyl chloroformate, etc. This reaction is carried out at a temperature of from about 0° C. to about 50° C., preferably about 25° C.

In accordance with the process of this invention, the C2 anion will not epimerize because it is tied back as a lactone and once the lactone is opened up, the carboxylate salt will suppress deprotonation at C2.

DESCRIPTION OF SPECIFIC EMBODIMENTS

In the following examples 1–6, melting points were recorded on a Thomas-Hoover capillary melting point apparatus and are uncorrected. Proton NMR spectra were recorded on Bruker WM 360 spectrometer using tetramethylsilane as an internal standard. Infrared spectra were determined on Nicolet 5DX FT IR spectrophotometer. Chromatographic separation was carried out using Woelm silica gel (0.040–0.063 mm) in flash chromatography or 0.5 mm E. Merck silica gel plates (60F.-254).

EXAMPLE 1 d,l cis-Ethyl 1,2,3,4-tetrahydro-6,7-methylenedioxy-4-oxo-1-(3,4,5-trimethoxyphenyl)naphthalen-2-carboxylate, (IVa), (Compound IV wherein $R^1$ and $R^2$, taken together, =methylenedioxy, $R^3=C_2H_5$, $R^4$ and $R^6=OCH_3$ and $R^5=CH_3$)

nBuLi solution in hexane (1.7M, 16.5 mL, 28 mmol) was added dropwise at $-78°$ C. to a solution of diisopropylamine (3.94 mL, 28 mmol) in 10 mL of THF. After 20 minutes of stirring at $-78°$ C., a THF solution of IIIa (compound III wherein $R^1$–$R^6$ are as defined in the title of this example) (3.0 g, 7.0 mmol) was added. The solution was warmed to $-40°$ C. for 1 hour and then treated with concentrated HCl solution (5 mL of concentrated HCl diluted to 10 mL with THF). The reaction mixture was diluted with ice water and extracted with ethyl acetate. Drying over $Na_2SO_4$ and removal of the solvent gave white solid. This was recrystallized from hot ethanol to give 2.11 g (70%) of the title compound; mp 146°–148° C.: NMR (CDCl$_2$) δ 1.22 (t, 3H, J=7 Hz), 2.74 (dd, 1H, J=18.1, 4.2 Hz), 2.93 (dd, 1H, J=18.0, 13.3 Hz), 3.72 (s, 6H), 3.80 (s, 3H), 4.10 (m, 2H), 4.66 (d, 1H, J=4.7 Hz), 6.03 (s, 1H), 6.04 (s, 1H), 6.17 (s, 2H), 6.62 (s, 1H), 7.54 (s, 1H); IR (KBr) 1731, 1674, 1590, 1504, 1481, 1255, 1130, 1038, cm$^{-1}$.

Anal. calcd. for $C_{23}H_{24}O_8.0.25H_2O$: C, 63.81; H, 5.70; Found: C, 63.59; H, 5.43.

EXAMPLE 2 d,l cis Ethyl (1,2-dihydro-6,7-methylenedioxy-4-trimethylsilyloxy-1-(3,4,5-trimethoxyphenyl)naphthalen-2-carboxylate, (Va), (Compound V wherein $R^1$ and $R^2$, taken together, =methylenedioxy, $R^3=C_2H_5$, $R^4$ and $R^6=OCH_3$, $R^5=CH_3$ and $R^7$, $R^8$ and $R^9=CH_3$ To a solution of IVa (856 mg, 2 mmol) in 10 mL of dry $CH_2Cl_2$ were added at 3° C. triethylamine (304 mg, 3 mmol) and trimethylsilyltrifluoromethanesulfonate (TMSOTf, 667 mg, 3 mmol). The mixture was stirred at room temperature for 1 hour. The mixture was cooled again and the same quantities of triethylamine and TMSOFf were added. The mixture was stirred at room temperature for 1 hour and then washed with cold saturated NaHCO$_3$ solution. The organic layer was dried over Na$_2$SO$_4$ and evaporated to give crude title compound. NMR (CDCl$_3$) δ 0.15 (m, 9H), 1.32 (t, 3H, J=7.321 Hz), 3.76 (s, 6H), 3.78 (s, 3H), 4.01 (m, 2H), 4.23 (1H, dd, J=7.439 Hz), 5.17 (d, 1H, J=2.776 Hz), 5.90 (d, 1H, J=9.623 Hz), 6.44 (s, 2H), 6.6 (s, 1H), 7.0 (s, 1H).

EXAMPLE 3 d,l [1α,2α,3β]-Ethyl-1,2,3,4-tetrahydro-3-benzyloxymethyl-4-oxo-1-(3,4,5-trimethoxyphenyl)naphthalen-2-carboxylate, (VIa) (Compound VI wherein $R^1$ and $R^2$, taken together, =methylenedioxy, $R^3=C_2H_5$, $R^5$ and $R^6=OCH_3$, $R^5=CH_3$ and $R^{10}=H$).

A. Crude Va obtained in Example 2 was re-dissolved in 5 mL of $CH_2Cl_2$ and added at $-20°$ C. to a solution of bisbenzyloxymethane (912 mg, 5 mmol) in 10 mL of $CH_2Cl_2$ containing 0.1 mL of the TMSOTf solution, (the TMSOTf solution was prepared by dissolving 10 g of TMSOTf in 10 mL of $CH_2Cl_2$). After stirring at room temperature for 18 hours, the reaction mixture was washed with saturated NaHCO$_3$ solution and dried over Na$_2$SO$_4$. Removal of the solvent and a SiO$_2$ chromatography of the residue (4% ethyl acetate-CH$_2$Cl$_2$) gave 613 mg (70% based on the recovered starting material, 170 mg) of the title compound, mp 107°–109° C.: NMR (CDCl$_3$) δ 1.19 (t, 3H, J=7 Hz), 2.99 (dt, 1H J=12.2 1 Hz), 3.63 (dd, 1H, J=9.2, 3.3 Hz), 3.71 (s, 6H), 3.78 (s, 3H), 3.83 (dd, 1H, J=12.5, 5.0 Hz), 4.01 (m, 2H), 4.30 (dd, 1H, J=9.0, 2.3 Hz), 4.36 (d, 1H, J=12.2 Hz), 4.50 (d, 1H, J=12.1 Hz), 4.56 (d, 1H, J=5.1 Hz), 6.01 (s, 1H), 6.02 (s, 1H), 6.10 (s, 2H), 6.59 (s, 1H), 7.29 (m, 5H), 7.55 (s, 1H); IR (KBr) 1733, 1672, 1590, 1560, 1532, 1250, 1130, 1035 cm$^{-1}$.

Anal. calcd. for $C_{31}H_{32}O_9.0.25H_2O$: C, 67.32; H, 5.92; Found: C, 67.24; H, 5.93.

B. To a solution of IVa (140 mg, 0.33 mmol) in 5 ml of $CH_2Cl_2$ were added at 0° C: triethylamine (55 μl, 0.40 mmol) and TMSOTf (80 μL, 0.40 mmol). After 0.5 hours of stirring at 0° C., the same quantities of triethylamine and TMSOTf were added. The reaction mixture was washed with saturated NaHCO$_3$ solution after 0.5 hours of additional stirring. The CH$_2$Cl$_2$ layer was dried over Na$_2$SO$_4$ and evaporated to give crude Va. This material was redissolved in 5 mL of CH$_2$Cl$_2$ and cooled to $-78°$ C. After addition of benzyloxymethyl chloride (100 mg, 0.8 mmol), TiCl$_4$ (44 μL, 0.4 mmol) was added dropwise. Stirring was continued at $-78°$ C. for one hour and at room temperature overnight. The reaction mixture was diluted with CH$_2$Cl$_2$ and washed with brine. The residue obtained after drying over Na$_2$SO$_4$ and evaporation of the solvent was chromatographed on SiO$_2$ (5% EtOAc-CH$_2$Cl$_2$) to give 85 mg of VIa (74% yield based on the recovered starting material, 50 mg). This material was identical to the product obtained in part A of this example by NMR and mass spectroscopy.

EXAMPLE 4 d,l [1α,2α,3β,4α]-Ethyl 1,2,3,4-tetrahydro-3-benzyloxymethyl-4-hydroxy-1-(3,4,5-trimethoxyphenyl)-naphthalene-2-carboxylate, (VIIa), (Compound VII wherein $R^1$ and $R^2$, taken together, =methylenedioxy, $R^3=C_2H_5$, $R^4$ and $R^6=OCH_3$, $R^5=CH_3$ and $R^{10}=H$) and Neopodophyllotoxin benzyl ether, (VIIIa), (Compound VIII wherein $R^1$ and $R^2$, taken together, =methylenedioxy, $R^3=C_2H_5$, $R^4$ and $R^6=OCH_3$, $R^5=CH_3$ and $R^{10}=H$)

To a solution of Compound VIa (400 mg, 0.55 mmol) in 5 mL of dry THF at 0° C. was added at 0.6 mL of LiBH$_4$ solution (2M in THF). After stirring at room temperature, the reaction was quenched by addition of a saturated NH$_4$Cl solution. The product was extracted with ethyl acetate, and the ethyl acetate layer was dried over $Na_2SO_4$. The residue obtained after evaporation of the solvent was chromatographed on $SiO_2$ plates (10% ethyl acetate-$CH_2Cl_2$) to give 120 mg (43%) of the second title compound, i.e., neopodophyllotoxin benzyl ether, mp 194°–196° C. NMR ($CDCl_3$) δ 2.96 (t, 1H, J=4.5 Hz), 3.25 (m, 1H), 3.39 (dd, 1H, J=7.9, 7.5 Hz), 3.55 (dd, 1H, J=7.4, 7.2 Hz), 3.71 (s, 6H), 3.83 (s, 3H), 4.10 (d, 1H, J=4.6 Hz), 4.45 (s, 1H), 5.16 (d, 1H, J=4.8 Hz), 5.96 (s, 2H), 6.21 (s, 2H), 6.42 (s, 1H), 6.71 (s, 1H), 7.29 (m, 5H); IR (KBr) 1775, 1590, 1508, 1485, 1330, 1255, 1125 cm$^{-1}$.

Anal. calcd. for $C_{29}H_{28}O_8 \cdot H_2O$: C, 66.65; H, 5.77; Found: C, 66.70; H 5.54.

A more polar band yielded 70 mg (25%) of the first title compound (VIIa), NMR ($CDCl_3$) δ 1.08 (t, 3H, J=7.1 Hz), 2.75 (m, 1H), 2.99 (dd, 1H, J=11.9, 5.4 Hz), 3.50 (t, 1H, J=8.5 Hz), 3.68–3.89 (m, 4H), 3.75 (s, 6H), 3.80 (s, 3H), 4.27 (d, 1H, J=5.5 Hz), 4.49 (d, 1H, J=12.0 Hz), 4.57 (d, 1H, J=12.0 Hz), 4.77 (d, 1H, J=7.7 Hz), 5.90 (s, 1H), 5.91 (s, 1H), 6.23 (s, 2H), 6.38 (s, 1H), 7.07 (s, 1H), 7.33 (m, 5H). Compound VIIa may be converted to Compound VIIIa in the presence of mild base.

EXAMPLE 5

Neopodophyllotoxin, (IXa), (Compound IX wherein $R^1$ and $R^2$, taken together, =methylenedioxy, $R^4$ and $R^6$=$OCH_3$ and $R^5$=$CH_3$)

A solution of compound VIIIa (80 mg, 0.16 mmol) in 10 mL of ethyl acetate containing a few drops of methanol and 40 mg of 10% Pd/C was hydrogenated under 30 psi of $H_2$ at room temperature for 3 hours. After filtration through celite the solvent was removed to give a white solid. This material was chromatographed on $SiO_2$ plates ($CH_2Cl_2$) to give 36 mg (55%) of the title compound, mp 235°–237° C.: NMR ($CDCl_3$ δ 3.02 (t, 1H, J=4.5 Hz), 3.17 (m, 1H), 3.67 (t, 1H, J=4.8 Hz), 3.76 (m, 1H), 3.78 (s, 6H), 3.85 (s, 3H), 4.25 (d, 1H, J=4.7 Hz), 5.18 (d, 1H, J=4.8 Hz), 5.95 (d, 1H, J=1.0 Hz), 5.97 (d, 1H, J=1.0 Hz), 6.27 (s, 2H), 6.49 (s, 1H), 6.74 (s, 1H); IR (KBr) 3425, 1764, 1592, 1508, 1489, 1333, 1255, 1240, 1125, 1037 cm$^{-1}$.

Anal. calcd. for $C_{22}H_{22}O_8 \cdot 0.5H_2O$: C, 62.40; H, 5.47; Found: C, 62.34; H, 5.22.

EXAMPLE 6

Podophyllotoxin, (Xa), (Compound X wherein $R^1$ and $R^2$, taken together, =methylenedioxy, $R^4$ and $R^5$=$OCH_3$ and $R^5$=$CH_3$)

Neopodophyllotoxin (IXa) (33 mg, 0.08 mmol) was dissolved in 1 mL of THF and 2 mL of water, and treated with 0.2 mL of 1N NaOH solution at room temperature for 2.5 hours. The resulting solution was cooled and acidified with 1N HCl solution. It was extracted rapidly with ethyl acetate and the ethyl acetate layer was washed with brine and dried over $Na_2SO_4$. The residue obtained after evaporation of the solvent was dissolved in 2 mL of dry THF and treated with dicyclohexylcarbodiimide (25 mg, 0.12 mmol) at an ice bath temperature for 2 hours. The resulting mixture was evaporated and chromatographed on $SiO_2$ plates (20% ethyl acetate-$CH_2Cl_2$) to give 15 mg (45% of the title compound; mp 234°–236° C. NMR ($CDCl_3$) δ 1.99 (d, 1H, J=8.1 Hz), 2.77–2.87 (m, 2H), 3.76 (s, 6H), 3.81 (s, 3H), 4.09 (t, 1H, J=9 z), 4.59 (d, 1H, J+5.1 Hz), 4.61 (t, 1H, J=6.9 Hz), 4.77 (t, 1H, J=8 Hz), 5.97 (d, 1H, J=1.2 Hz), 5.98 (d, 1H, J=1.2 Hz), 6.37 (s, 2H), 6.51 (s, 1H), 7.11 (s, 1H); IR (KBr) 3420, 1765, 1592, 1508, 1485, 1240, 1130 cm$^{-1}$.

Anal. calc'd. for $C_{22}H_{22}O_8 \cdot 0.25H_2O$: C, 63.08; H, 5.41; Found: C, 63.00; H, 5.33.

We claim:
1. A compound of the formula

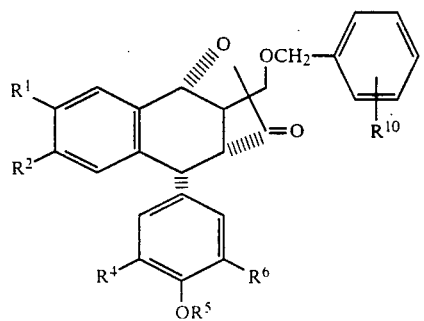

VIII wherein $R^1$ and $R^2$ each are independently hydrogen or (lower)alkoxy, or $R^1$ and $R^2$, taken together, is methylenedioxy; $R^4$ and $R^6$ each are independently hydrogen or (lower)alkoxy; $R^5$ is hydrogen or a phenol-protecting group; and $R^{10}$ is hydrogen, lower(alkyl), lower(alkoxy) or nitro.

2. A compound as defined in claim 1 wherein $R^1$ and $R^2$, taken together, is methylenedioxy; $R^4$ and $R^6$ are each methoxy; $R^5$ is methyl; and $R^{10}$ is hydrogen.

* * * * *